(12) United States Patent
Nonaka

(10) Patent No.: US 10,939,886 B2
(45) Date of Patent: Mar. 9, 2021

(54) RADIATION IMAGING APPARATUS, RADIATION IMAGING SYSTEM, RADIATION IMAGING METHOD, AND COMPUTER-READABLE MEDIUM

(71) Applicant: CANON KABUSHIKI KAISHA, Tokyo (JP)

(72) Inventor: Hideki Nonaka, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 185 days.

(21) Appl. No.: 15/820,583

(22) Filed: Nov. 22, 2017

(65) Prior Publication Data

US 2018/0146943 A1 May 31, 2018

(30) Foreign Application Priority Data

Nov. 28, 2016 (JP) .............................. JP2016-230335

(51) Int. Cl.
*A61B 6/00* (2006.01)
(52) U.S. Cl.
CPC .............. *A61B 6/5205* (2013.01); *A61B 6/42* (2013.01); *A61B 6/586* (2013.01); *A61B 6/502* (2013.01); *A61B 6/563* (2013.01)
(58) Field of Classification Search
None
See application file for complete search history.

(56) References Cited

U.S. PATENT DOCUMENTS

| 2011/0150182 | A1* | 6/2011 | Omura ................. | A61B 6/4405 |
| | | | | 378/98.5 |
| 2015/0078527 | A1* | 3/2015 | Iwamoto ................ | A61B 6/563 |
| | | | | 378/91 |
| 2015/0365551 | A1* | 12/2015 | Panuganti .......... | H04N 1/00973 |
| | | | | 358/1.15 |
| 2016/0135764 | A1* | 5/2016 | Wojcik ................. | A61B 6/4233 |
| | | | | 378/62 |
| 2017/0311920 | A1* | 11/2017 | Hiroshige .............. | A61B 6/468 |

FOREIGN PATENT DOCUMENTS

| JP | 3302163 B2 | 7/2002 |
| JP | 2007522894 A | 8/2007 |
| JP | 5649635 B2 | 1/2015 |
| JP | 5665901 B2 | 2/2015 |
| JP | 5697732 B2 | 4/2015 |
| JP | 2016101210 A | 6/2016 |

OTHER PUBLICATIONS

Japanese Office Action dated Oct. 27, 2020, for Corresponding Japanese Application No. 2016230335.

* cited by examiner

*Primary Examiner* — Hoon K Song
(74) *Attorney, Agent, or Firm* — Carter, DeLuca & Farrell LLP

(57) ABSTRACT

A radiation imaging apparatus is provided that includes: a radiation detection unit arranged to detect radiation; a generation unit configured to generate a radiation image based on the detected radiation; a storage configured to store a plurality of radiation images; a detection unit configured to detect one of a failure in and impossibility of one of taking of the radiation image and storing of the radiation image in the storage; and a communication unit configured to establish communication with an external apparatus when one of the failure and the impossibility is detected.

16 Claims, 5 Drawing Sheets

RADIATION IMAGING APPARATUS, RADIATION IMAGING SYSTEM, RADIATION IMAGING METHOD, AND COMPUTER-READABLE MEDIUM

BACKGROUND OF THE INVENTION

Field of the Invention

The present invention relates to a radiation imaging apparatus, a radiation imaging system, a radiation imaging method, and a computer-readable medium.

Description of the Related Art

As a radiation imaging apparatus used for medical image diagnosis and non-destructive inspection, a radiation imaging apparatus that includes a matrix substrate made up of a pixel array in which switches, such as TFTs, and conversion elements, such as photoelectric conversion elements, are combined is put into practical use.

Such a radiation imaging apparatus can be easily handled, and has a reduced size and weight. An internal battery is adopted as a power source of such a radiation imaging apparatus, and a scheme of communication with the outside is adopted as a wireless communication. This configuration omits a cable for connection to the apparatus, and improves the apparatus handling and the flexibility of imaging procedures.

A radiation imaging apparatus that includes a light shielding case that accommodates a conventional film and an intensifying screen is called a "film cassette". A radiation imaging apparatus that operates through controlling the pixel array by an electronic circuit is called an "electronic cassette". The electronic cassette is disclosed in Japanese Patent No. 3,302,163.

The electronic cassette different from the film cassette has characteristics capable of displaying a radiation image immediately after taking the radiation image. For example, a console capable of displaying a radiation image and the electronic cassette are connected to each other through wireless communication. This configuration can transfer data to the console immediately after the radiation image is taken by the electronic cassette, and allow the console to display the radiation image immediately after imaging. The technique is disclosed in Japanese Patent No. 5,697,732.

The electronic cassette different from the film cassette has characteristics that can store multiple radiation images in a storage in the radiation imaging apparatus without any need to replace the film. In particular, the electronic cassette itself can preliminarily take and store the radiation images without establishment of communication with the console, thereby achieving easy handling of the electronic cassette.

For example, multiple radiation images taken in a state without establishment of communication with the console are stored in the storage in the radiation imaging apparatus. After the communication with the console is manually established, the radiation images stored in the storage are data-transferred to the console, thereby allowing the console to display the radiation images.

However, according to the conventional electronic cassette, if the capacity of a storage area for storing the radiation images becomes insufficient in a state without establishment of communication to the console, the electronic cassette can neither data-transfer the radiation images to the console nor store the images in the storage. Furthermore, according to the conventional electronic cassette, in case the components of the electronic cassette malfunction owing to a failure in a state without establishment of communication with the console, it is difficult for an operator to know the malfunctioning and its cause (the failure site, environment of usage, and usage situations).

SUMMARY OF THE INVENTION

A radiation imaging apparatus according to one embodiment of the present invention includes: a radiation detection unit arranged to detect radiation; a generation unit configured to generate a radiation image based on the detected radiation; a storage configured to store a plurality of radiation images; a detection unit configured to detect one of a failure in and impossibility of one of taking of the radiation image and storing of the radiation image in the storage; and a communication unit configured to establish communication with an external apparatus when one of the failure and the impossibility is detected.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

Figure 1:
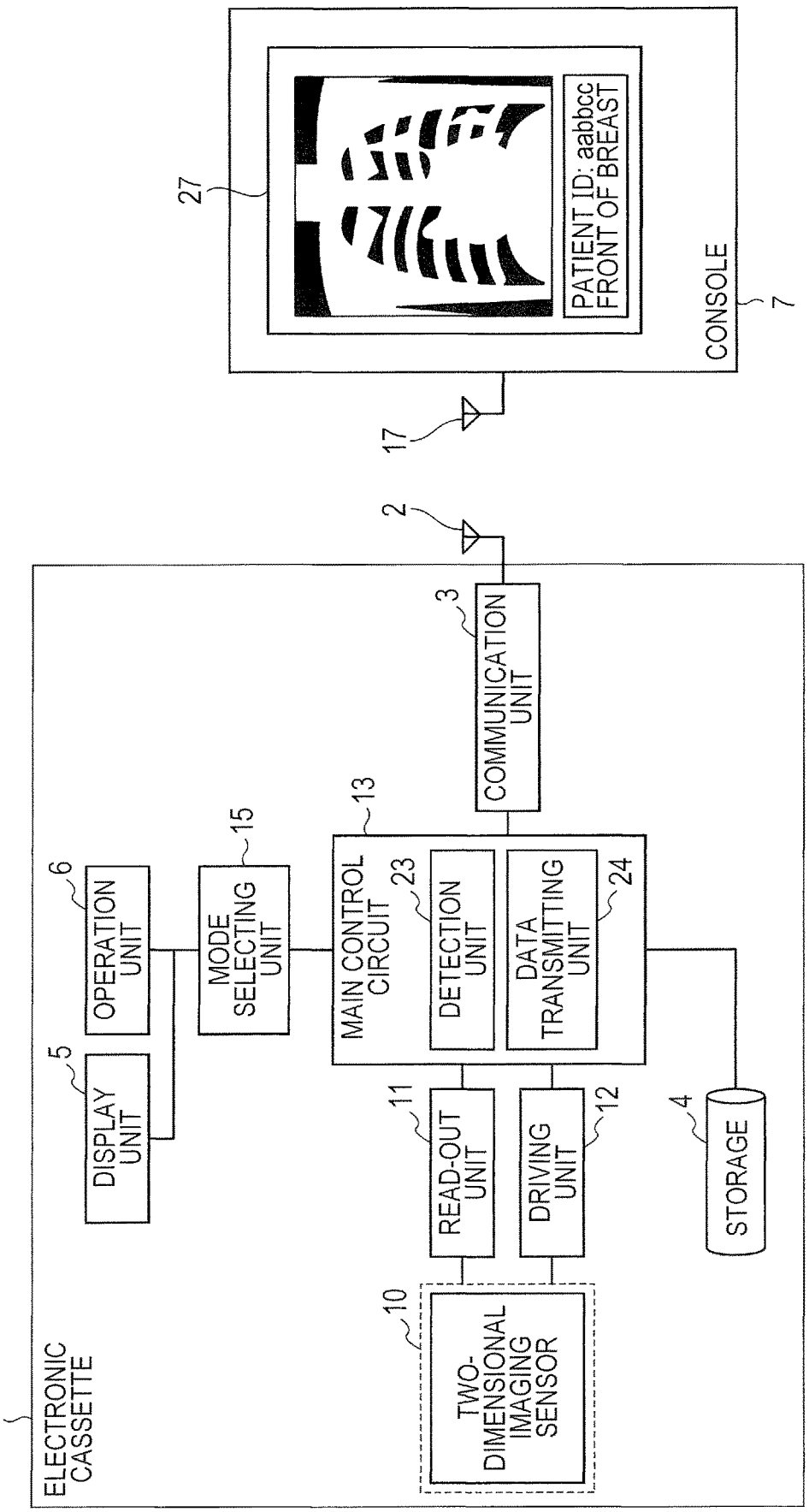
FIG. 1 is a block diagram illustrating a configuration example of a radiation imaging system of the present invention.

FIG. 1 is a block diagram illustrating one example of a radiation imaging system of this embodiment. FIG. 1 illustrates an electronic cassette (radiation imaging apparatus) 1 that generates a radiation image based on radiation, and a console 7 that wirelessly communicates with the electronic cassette 1.

The electronic cassette 1 includes a communication interface 2, a communication unit 3, a storage 4, a display unit 5, an operation unit 6, a two-dimensional imaging sensor (radiation detection unit) 10, a read-out circuit 11, a driving circuit 12, a main control circuit 13, and a mode selecting unit (switch unit) 15. The main control circuit includes a detection unit 23, and a data transmitting unit 24. The console 7 includes a communication interface 17, and a display unit 27. The console 7 controls a radiation generator (not illustrated) that generates radiation, and the electronic cassette 1.

Communication between the electronic cassette 1 and the console 7 is established via the communication interfaces 2, 17 through wireless LAN communication of e.g. IEEE 802.11 standard. In the console 7, the state of the electronic cassette 1 in communication with the console 7 (for example, whether to be in an energy saving standby state or not, and whether to have already completed imaging preparation or not) is displayed on the display unit 27.

The electronic cassette 1 can be controlled by an operation through the console 7. Radiation images acquired by irradiating the electronic cassette 1 with radiation (e.g., X-rays) are data-transferred to the console 7 having established communication with the electronic cassette 1 and are displayed on the display unit 27 of the console 7. As a result, the operator can confirm the radiation images on the display unit 27 of the console 7.

According to this embodiment, the console 7 internally includes a communication unit (not illustrated). Note that in a case where a wireless station that establishes wireless communication with the electronic cassette 1 resides separately from the console 7, and the wireless station and the console 7 are connected to each other through wired communication (e.g., a wired network line), the communication unit is not necessarily included. The electronic cassette 1 and the console 7 may establish communication through wireless communication, or through wired communication instead. For example, the electronic cassette 1 and the console 7 may be connected directly or through a network switch via a wired network line.

In a case where a radiation image is taken using radiation, the timing of irradiation by the radiation generation apparatus with radiation and the imaging operation of the electronic cassette 1 is described. A mode, in which the two-dimensional imaging sensor (pixel array) 10 of the electronic cassette 1 detects radiation with which the electronic cassette 1 is irradiated and an image receiving circuit is passively controlled to thereby take a radiation image, is called a "asynchronous mode". On the other hand, a mode, in which in response to an irradiation request issued by the radiation generation apparatus, the electronic cassette 1 responds with an irradiation permission to thereby actively establish timing synchronization between irradiation with radiation and imaging, is called a "synchronous mode".

Communication of timing control in the synchronous mode (transmission and reception of the irradiation request and the irradiation permission) is achieved through intervention of communication by the console 7 between the radiation generation apparatus and the electronic cassette 1. For example, the radiation generation apparatus and the console 7 are connected to each other through wired communication, and the console 7 and the electronic cassette are connected to each other through one of wireless communication and wired communication, thereby achieving timing control.

A wireless station that establishes wireless communication with the electronic cassette 1 may reside separately from the console 7, and the wireless station, the console 7 and the radiation generation apparatus may be connected to each other through wired communication (a wired network line). The electronic cassette 1, the console 7 and the radiation generation apparatus may be connected directly or through a network switch via a wired network line.

As described above, the operation mode, in which the electronic cassette 1 establishes communication with the console 7, and takes a radiation image while operating as a node in a network, is called the network mode.

Figure 2:
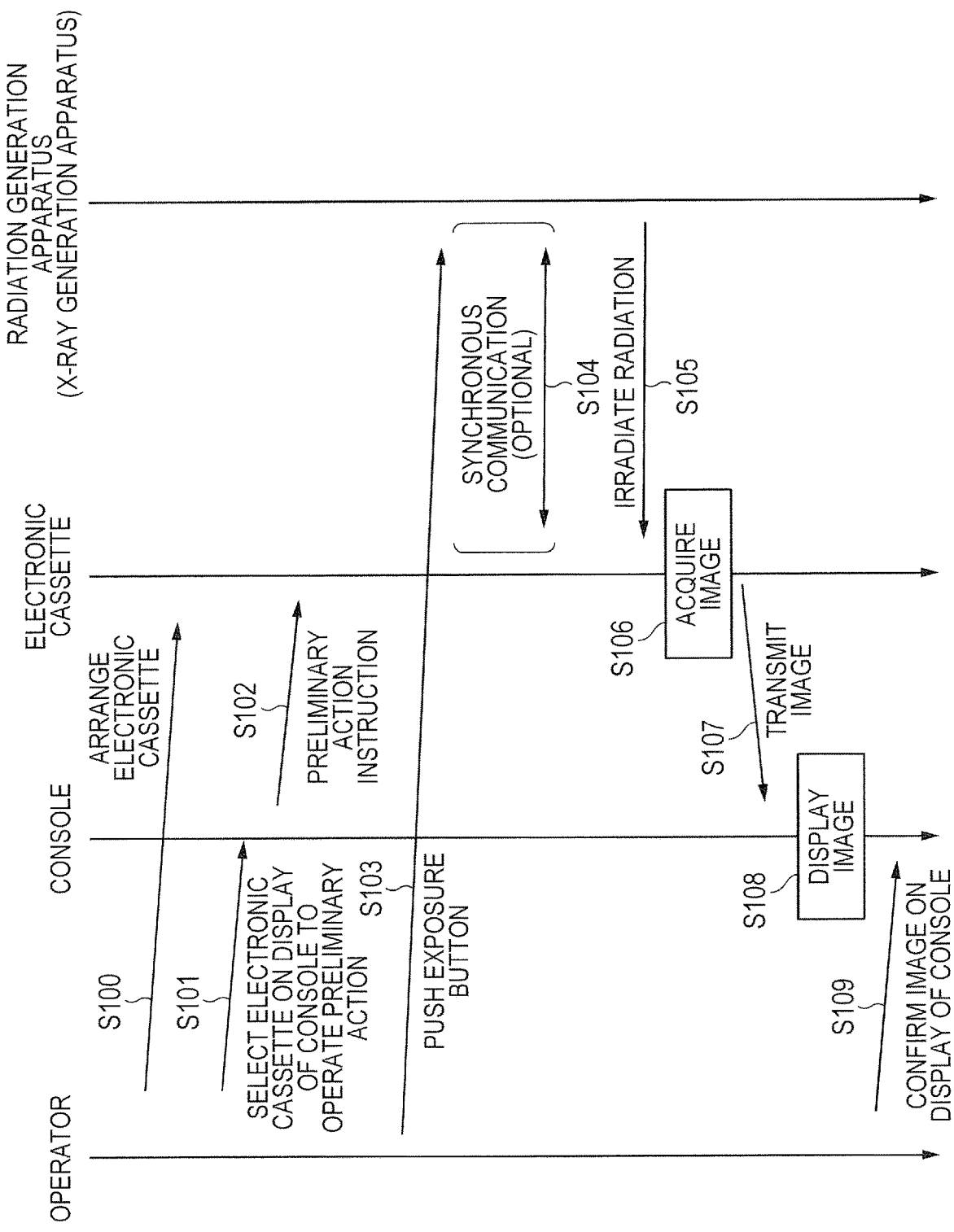
FIG. 2 is a diagram illustrating an operation of the radiation imaging apparatus of the present invention in a network mode.

An example where in the network mode, the electronic cassette 1, the console 7 and the radiation generation apparatus operate in a collaborative manner through an operation by the operator is described with reference to FIG. 2.

First, the operator arranges the electronic cassette 1 according to the position and attitude of a subject, and adjusts a radiation tube of the radiation generation apparatus toward the subject (step S100). Next, the operator selects the electronic cassette 1 on the display unit 27 of the console 7 to issue an instruction of causing the electronic cassette 1 to perform preliminary action (step S101). The console 7 confirms the state of the electronic cassette 1 and executes a preliminary action instruction as required (step S102). The preliminary action includes scanning for discharging dark current from the electronic cassette 1.

When the preliminary action is executed and the electronic cassette 1 reaches a steady state, the operator pushes an exposure button (irradiation switch) provided for the radiation generation apparatus (step S103).

Since dark current occurs in the pixel array in the electronic cassette 1, the operation timing of the radiation generation apparatus and the electronic cassette 1 may be synchronized, to utilize radiation to the maximum while reducing the adverse effects of dark current (step S104).

For example, while the electronic cassette 1 takes no image, scanning for discharging dark current from the pixel array is repeatedly performed. On the other hand, during the radiation generation apparatus emits radiation and the electronic cassette 1 performs the imaging, scanning for discharging current is stopped so as not to emit the charges due to detected radiation. According to this configuration, the electronic cassette 1 directly or indirectly communicate not only with the console 7 but also with the radiation generation apparatus, and is controlled in the synchronous mode. The protocol used therefor is disclosed in Japanese Patent No. 5,649,635.

A case where timing synchronization between the electronic cassette 1 and the radiation generation apparatus is not required and control in the asynchronous mode is performed is disclosed in Japanese Patent No. 5,665,901.

By the exposure button (irradiation switch) being pushed, the radiation generation apparatus generates and emits radiation to irradiate the subject and the electronic cassette 1 with the radiation (step S105).

After irradiation with radiation, the read-out circuit 11 of the electronic cassette 1 reads the pixel array, generates digital data (radiation image data) based on the radiation detected by the pixel array (step S106), and transmits the data to the console 7 (step S107). The console 7 displays the received radiation image on the display unit (step S108), and allows the operator to confirm the radiation image (step S109).

For operation in the network mode, predetermined parameter setting is required in the electronic cassette 1. For example, an identification code of an apparatus that communicates with the electronic cassette 1, key information on communication encryption, a type of synchronous mode/asynchronous mode, and an address value of an apparatus that communicates with the electronic cassette 1 in the synchronous mode are set.

In this embodiment, these parameters are input through the display unit 5 and the operation unit 6 of the electronic cassette 1. However, the configuration is not limited thereto. For example, the parameters may be set via a short range wireless communication means (not illustrated) from the console 7 when the electronic cassette 1 approaches the console 7. The parameters may be set by wired connection between the electronic cassette 1 and the console 7 through a wired network line. The parameters to be set are not limited to the communication parameters described above. For example, an identification code (e.g., the name of apparatus) may be set that allows the operator to identify an apparatus that communicates with the electronic cassette 1.

The operation in the network mode is performed by collaboration between the electronic cassette 1, the console 7 and the radiation generation apparatus.

Figure 3:
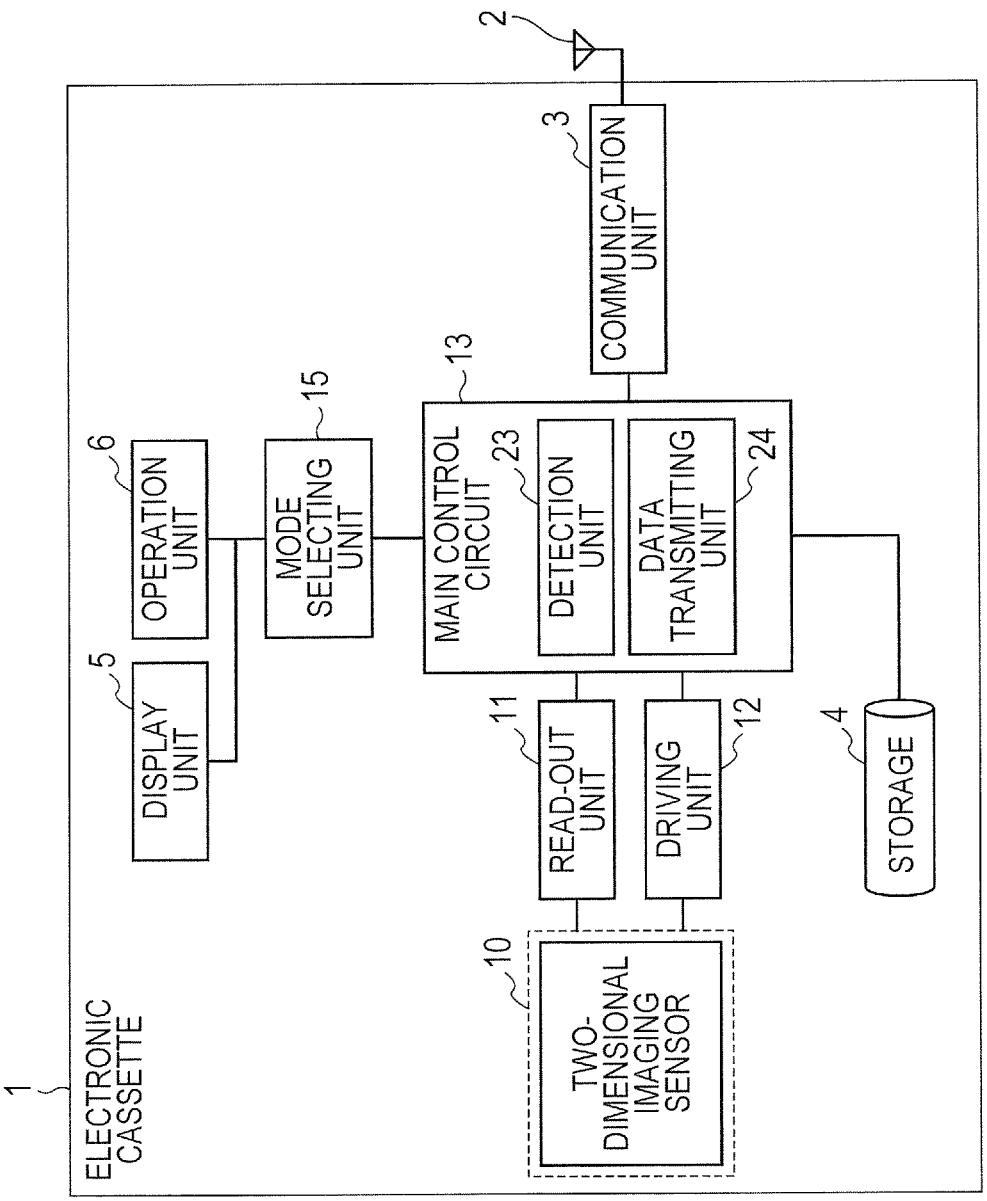
FIG. 3 is a block diagram illustrating a configuration example of a radiation imaging apparatus of the present invention.

On the other hand, the electronic cassette 1 may operate in a mode of taking a radiation image in a state where no communication is established with the console 7. This mode is called the standalone mode. FIG. 3 is a block diagram illustrating a configuration example of the electronic cassette 1 in the standalone mode.

In the standalone mode, the electronic cassette 1 does not communicate with the outside during execution of taking a radiation image. Accordingly, the electronic cassette 1 neither communicates with the console 7 nor communicates with the radiation generation apparatus for timing synchronization. Consequently, the storage 4 in the electronic cassette 1 stores the taken radiation image. Timing synchronization between the electronic cassette 1 and the radiation generation apparatus is not required, and control is performed in the asynchronous mode.

A conventional film cassette does not require the console 7, and is easily handled. In the standalone mode of the electronic cassette 1, the electronic cassette 1 itself can take and store a radiation image without establishing communication with the console 7. Accordingly, the ease of handing can be improved also in the electronic cassette 1.

In comparison with the film cassette according to which a film is required to be taken out and developed every time of imaging, the electronic cassette 1 can consecutively take multiple radiation images, and store the multiple radiation images in the internal storage 4 (such as an image memory).

In the standalone mode, multiple radiation images are consecutively taken using the radiation generation apparatus and the electronic cassette 1, and wireless communication is established between the electronic cassette 1 and the console 7, thereby the standalone mode switched to the network mode. Subsequently, the radiation images stored in the storage 4 are transferred to the console 7. The transferred radiation images are displayed by the console 7, which allows the operator to observe the radiation images.

A "semi-autonomous" radiation imaging apparatus has been proposed where instead of the console 7, a portable information terminal (not illustrated) accepts subject information and imaging order information, and issues an imaging instruction to the electronic cassette 1. A "fully autonomous" radiation imaging apparatus where the electronic cassette 1 itself executes imaging has been proposed.

Figure 4:
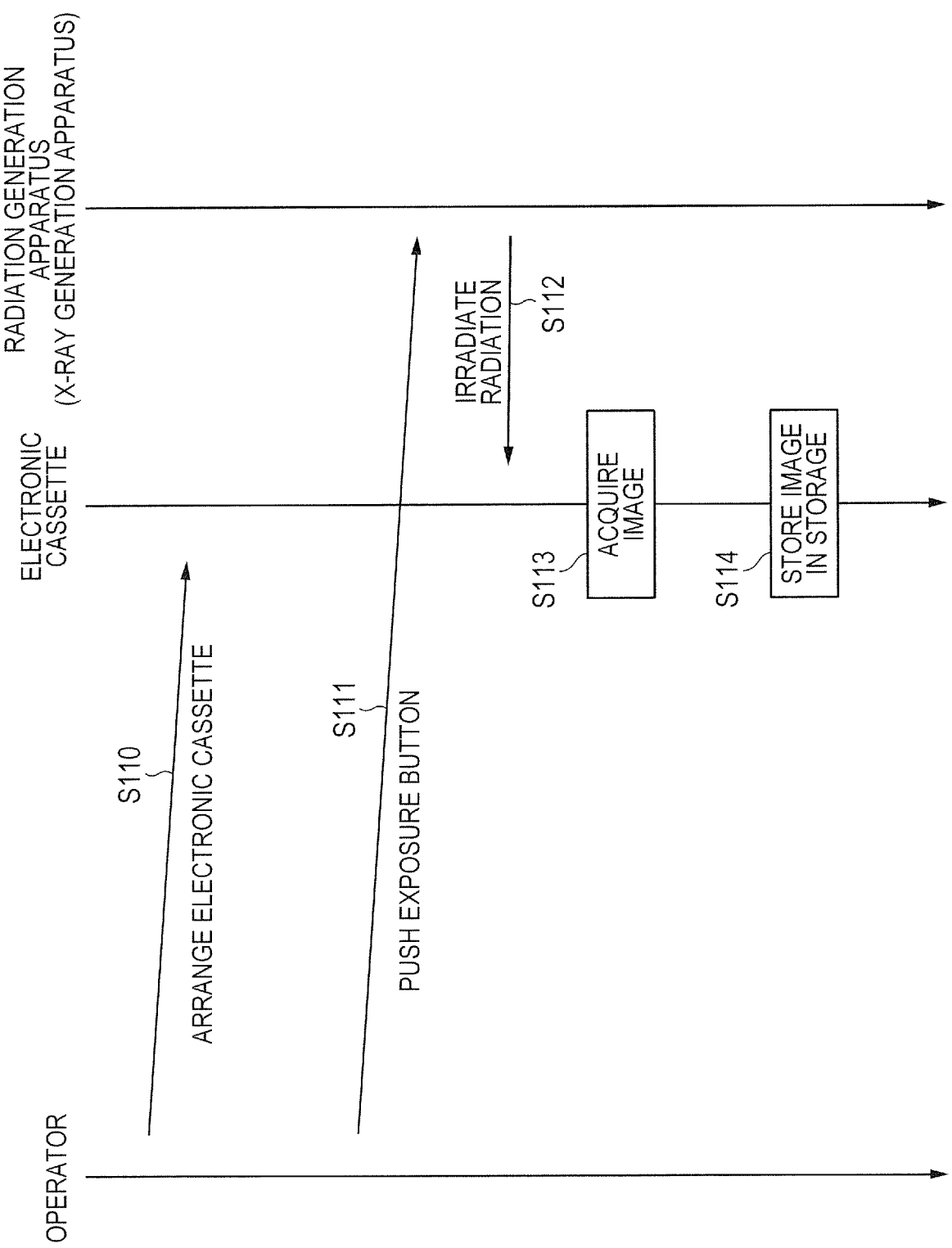
FIG. 4 is a diagram illustrating an operation of the radiation imaging apparatus of the present invention in a standalone mode.

Referring to FIG. 4, the fully autonomous radiation imaging apparatus is described. First, the operator arranges the electronic cassette 1 with respect to the subject, and adjusts the radiation tube (X-ray tube) toward the subject (step S110). The preliminary action of the electronic cassette 1 is started by operating the electronic cassette 1 when the electronic cassette 1 is arranged. When the electronic cassette 1 reaches a steady state by the preliminary action, the operator pushes the exposure button (irradiation switch) provided for the radiation generation apparatus (step S111). Accordingly, radiation is emitted from the radiation generation apparatus toward the subject and the electronic cassette 1 (step S112). In the standalone mode, imaging is performed in the asynchronous mode. While the two-dimensional imaging sensor (pixel array) 10 of the electronic cassette 1 detects the radiation, with which the electronic cassette 1 is irradiated, passively controls the image receiving circuit, and the electronic cassette 1 performs imaging, scanning for discharging charges is stopped so as not to discharge the charges due to the detected radiation.

After irradiation with radiation, the read-out circuit 11 of the electronic cassette 1 reads the pixel array, generates radiation image (step S113), and stores the radiation image in the storage 4 in the electronic cassette (step S114). The electronic cassette 1 repeats the radiation image taking and storing. After the electronic cassette 1 establishes communication with one of the console 7 and a workstation for observing the radiation image, the radiation image stored in the storage 4 is transferred to one of the console 7 and the workstation. After the communication with one of the console 7 and the workstation (external apparatus) is established, the communication unit can communicate with one of the console 7 and the workstation (external apparatus) via a network in a hospital. A radio frequency band different from the band in which the radiation imaging apparatus and one of the console 7 and the workstation (external apparatus) directly communicate with each other can be used as the radio frequency band of the network in the hospital in this case.

The standalone mode and the network mode of the electronic cassette 1 can be freely switched according to the operator's usage and request, and the operation can be achieved.

For example, in a case where the electronic cassette 1 is used in combination with a stationary radiation generation apparatus in an imaging room of a radiology department in a hospital, the electronic cassette 1 is operated in the network mode and the synchronous mode in combination with the console 7 installed in the same imaging room.

In a case where the electronic cassette 1 is temporarily taken to the outside and used outside of the imaging room, the electronic cassette 1 is mounted on a radiation generation apparatus for round visits, and the electronic cassette 1 is operated in the standalone mode and the asynchronous mode. Alternatively, a portable radiation generation apparatus that can be more easily carried than that for round visits, and the electronic cassette 1 may be taken out of the imaging room, and the electronic cassette 1 may be operated in the standalone mode and the asynchronous mode.

After the electronic cassette 1 takes a radiation image outside of the imaging room, this cassette is carried back to the imaging room and the standalone mode is switched to the network mode. In the operation of switching the operation mode from the standalone mode to the network mode, it is important to set the operation mode of the electronic cassette 1 correctly.

In the electronic cassette 1 in this embodiment, the network mode is manually switched to the standalone mode by the operator. The operator issues an instruction of switching the operation mode, through the display unit 5 and the operation unit 6, which are included in the electronic cassette 1. In view of preventing an erroneous operation, the operation mode can be switched by simultaneous execution of two or more operations (e.g., an operation of simultaneously pushing two buttons) or execution of a combination of two or more operation procedures (e.g., an operation of pushing a button A and subsequently pushing a button B).

In the standalone mode, the electronic cassette 1 is operated in the semi-autonomous type or fully autonomous type operation mode. The operation unit 6 for switching the operation mode can be included in one of the electronic cassette 1 and the portable information terminal so as to allow the operation mode to be switched after the operator takes the electronic cassette 1 to the outside for use in the standalone mode. In this case, the operation unit 6 switches the operation mode of the electronic cassette 1 from the network mode to the standalone mode. The operation unit 6 may switch the operation mode of the electronic cassette 1 from the standalone mode to the network mode.

In the standalone mode, the communication between the electronic cassette 1 and the console 7 is disabled, and the communication is disconnected. Consequently, also in a case where a radiation image is taken at a location where wireless communication is prohibited, the radiation image can be taken by operating the electronic cassette 1 in the standalone mode.

In the case where the electronic cassette 1 is operated in the standalone mode, the electronic cassette 1 is operated in the asynchronous mode, where radiation with which the electronic cassette 1 is irradiated is detected and the image receiving circuit is passively controlled. The taken radiation image is stored in the storage 4 in the electronic cassette 1. The communication with the console is disabled while the standalone mode is maintained. Consequently, the radiation image and the other information related to taking images are not transmitted to the outside immediately after imaging. The operations of taking and storing the radiation image are repetitively executed while the standalone mode is maintained. The radiation images are sequentially stored in the storage 4.

In the standalone mode, the communication with the console 7 is disabled. Accordingly, for transfer of the taken radiation images to the console 7, the communication between the console 7 and the electronic cassette 1 is required to be established. Consequently, the mode of the electronic cassette 1 is automatically switched from the standalone mode to the network mode by enabling the communication with the console 7. When the electronic cassette 1 detects a connection signal for allowing the electronic cassette 1 and the console 7 to establish communication, the mode of the electronic cassette 1 is automatically switched from the standalone mode to the network mode.

For example, in a case where communication between the electronic cassette 1 and the console 7 is established through wired communication, a communication cable is connected to the connectors of the electronic cassette 1 and the console 7, and the communication is enabled. When the detection unit 23 detects the connection of the communication cable to the connector as a connection signal, the mode of the electronic cassette 1 is automatically switched from the standalone mode to the network mode.

In a case where communication between the electronic cassette 1 and the console 7 is established through wireless communication, a parameter for wireless communication is set in the electronic cassette 1, and the communication is enabled. When the detection unit 23 detects the setting of the parameter as a connection signal, the mode of the electronic cassette 1 is automatically switched from the standalone mode to the network mode.

As described above, the detection unit 23 detects connection by one of wired communication and wireless communication to the console 7 (external apparatus). When the connection is detected, the communication unit 3 establishes communication with the console 7 (external apparatus). Upon detection by the detection unit 23, the mode selecting unit 15 switches the standalone mode (first operation mode) capable of taking the radiation image without establishing communication with the console 7, to the network mode (second operation mode) capable of establishing communication with the console 7. After the communication with the console 7 (external apparatus) is established, the communication unit 3 can communicate with one of the console 7 and the workstation (external apparatus) via the network in the hospital. A radio frequency band different from the band in which the radiation imaging apparatus and the console (external apparatus) directly communicate with each other can be used as the radio frequency band in the hospital in this case.

In a case where repetition of the radiation image taking and storing in the standalone mode makes the available capacity of the storage area of the storage 4 insufficient and the radiation image cannot be stored in the storage 4, the radiation images stored in the storage 4 are required to be transferred to the console 7. Accordingly, the main control circuit 13 detects the insufficient available capacity of the storage 4, and the mode selecting unit 15 switches the operation mode from the standalone mode to the network mode.

More specifically, the detection unit 23 detects that the radiation image storing is to be failed or impossible owing to the insufficient available capacity. When the failure in or impossibility of radiation image storing is detected, the communication unit 3 establishes communication with the console 7 (external apparatus). Upon detection by the detection unit 23, the mode selecting unit switches the standalone mode (first operation mode) capable of taking the radiation image without establishing communication with the console 7, to the network mode (second operation mode) capable of establishing communication with the console 7. In other words, the detection unit 23 detects the state of the electronic cassette 1, and the communication unit 3 establishes communication with the console 7 according to the state of the electronic cassette 1.

Upon detection by the detection unit 23, the data transmitting unit 24 transmits at least one of storage failure information that indicates one of the failure in and impossibility of the radiation image storing, capacity information that indicates the capacity of the storage 4, and the radiation image stored in the storage 4, to the console 7 (external apparatus).

Figure 5:
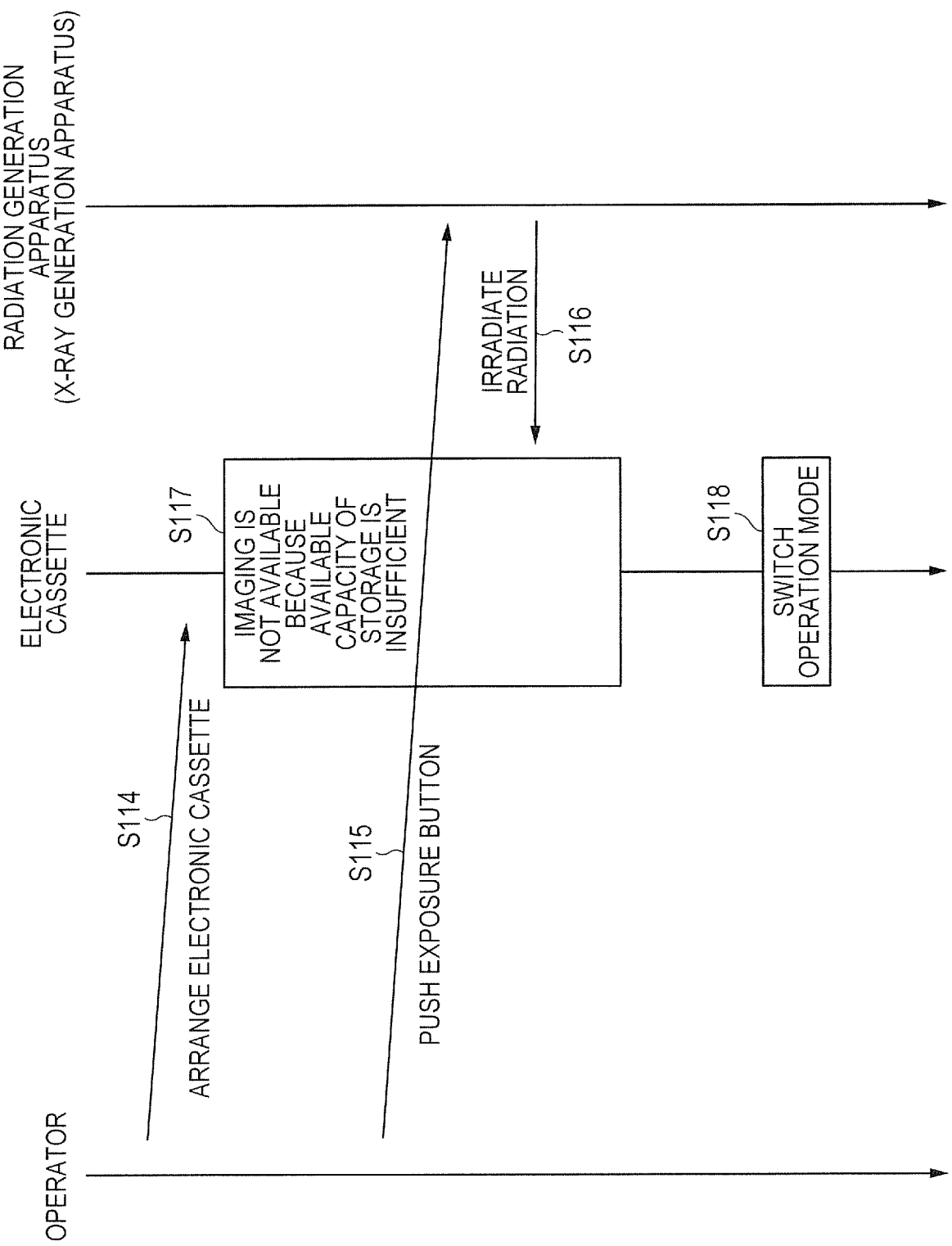
FIG. 5 is a diagram illustrating operation mode switching in the radiation imaging apparatus of the present invention in a case where the available capacity of a storage is insufficient.

FIG. 5 is a flowchart indicating the operation of the electronic cassette 1 in a case where the electronic cassette 1 is set to be in the standalone mode and the available capacity is insufficient in the storage 4. In the standalone mode, the electronic cassette 1 does not communicate with the outside. Consequently, the state of the electronic cassette 1 is confirmed on the display unit 5 of the electronic cassette 1.

First, the operator arranges the electronic cassette 1 with respect to the subject, and adjusts the radiation tube (X-ray tube) toward the subject (step S114). In a case where the number of taken radiation images is not confirmed on the display unit 5 when the operator arranges the electronic cassette 1, the available capacity of the storage 4 sometimes becomes insufficient and the electronic cassette 1 is in a state incapable of receiving the image (one of the failure in and impossibility of radiation image storing).

In this case, the operator pushes the exposure button (irradiation switch) provided for the radiation generation apparatus (step S115). Even if the radiation generation apparatus emits radiation toward the subject and the electronic cassette 1 (step S116), the electronic cassette 1 can neither generate the radiation image nor store the radiation image in the storage 4 (step S117).

Conventionally, the operator cancels the arrangement of the electronic cassette 1, confirms the number of taken radiation images on the display unit 5, manually switches the mode to the network mode, and transmits the radiation images to the console 7, thereby securing the available capacity of the storage 4. In this embodiment, the detection unit 23 of the main control circuit 13 detects the insufficient available capacity of the storage 4, and the mode selecting unit 15 automatically switches the operation mode from the standalone mode to the network mode (step S118). Subsequently, the available capacity of the storage 4 is secured by manually or automatically transmitting the radiation images to the console 7.

In a case where the function of the device included in the electronic cassette 1 malfunctions to cause an operation error according to which it is difficult to continue the operation of the electronic cassette 1 in the standalone mode, the operator is required to notice the malfunctioning and its cause (the failure part, environment of usage, and usage situations). At this time, the electronic cassette 1 establishes communication with the external error analysis apparatus (e.g., the console 7), and issues a notification about the operation error and analyzes this error. According to information displayed on the display unit 5 in a state where the external communication is disabled, the details of the cause of the operation error cannot be determined.

Accordingly, the main control circuit 13 detects the malfunctioning, and the mode selecting unit 15 switches the operation mode from the standalone mode to the network mode.

More specifically, the detection unit 23 detects that the radiation image taking is failed or impossible. When the failure in or impossibility of radiation image taking is detected, the communication unit 3 establishes communication with the console 7 (external apparatus). Upon detection by the detection unit 23, the mode selecting unit switches the standalone mode (first operation mode) capable of taking the radiation image without establishing communication with the console 7, to the network mode (second operation mode) capable of establishing communication with the console 7. In other words, the detection unit 23 detects the state of the electronic cassette 1, and the communication unit 3 establishes communication with the console 7 according to the state of the electronic cassette 1.

Upon detection by the detection unit 23, the data transmitting unit 24 transmits at least one of imaging failure information that indicates the failure in or impossibility of the radiation image taking, and cause information that indicates the cause of the failure in or impossibility of radiation image taking, to the console 7 (external apparatus).

When the electronic cassette 1 is operated in the standalone mode, an internal power source, such as a battery, is used. To achieve a long-time operation of the electronic cassette 1, the electronic cassette 1 is in a sleep state (a state where the power is turned off) in a non-use time during which the operator does not use the electronic cassette 1.

When the power is turned on again, the electronic cassette 1 can be operated as it is in the standalone mode without switching the operation mode. Accordingly, the storage 4 stores the operation mode before the power is turned off. When the power is turned on again, the mode selecting unit 15 of the electronic cassette 1 reads the operation mode before turning off of the power from storage 4 and recovers in the standalone mode before turning off of the power. In a case where the operation mode before turning off of the power is the network mode, the mode selecting unit 15 of the electronic cassette 1 may read the operation mode before turning off of the power from the storage 4 and recovers in the network mode before turning off of the power.

The storage 4 stores the operation mode that is a mode when the power supplied to the electronic cassette 1 (radiation imaging apparatus) is turned off (one of the first operation mode and the second operation mode). The mode selecting unit (switch unit) 15 maintains the stored operation mode, when the power supply to the electronic cassette 1 is restarted.

As described above, the electronic cassette 1 in this embodiment can automatically switch the operation mode when a predetermined condition is satisfied, thereby improving the convenience of the operation of the electronic cassette (radiation imaging apparatus) 1.

According to the embodiment described above, the radiation imaging apparatus that can automatically switch the operation mode when the predetermined condition is satisfied can be provided, thereby improving the convenience of the operation of the radiation imaging apparatus.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-230335, filed Nov. 28, 2016, which is hereby incorporated by reference herein in its entirety.

What is claimed is:

1. A radiation imaging apparatus comprising:
a radiation detector arranged to detect radiation;
one or more processors; and
a memory including instructions stored thereon that, when executed by the one or more processors, cause the radiation imaging apparatus to function as:
a generation unit configured to generate a radiation image based on the detected radiation;
a storage configured to store a plurality of radiation images;

a detection unit configured to detect one of a failure in and impossibility of one of taking of the radiation image and storing of the radiation image in the storage; and a setting unit configured to set a parameter for wireless communication in the radiation imaging apparatus to set the radiation imaging apparatus in a second operation mode of establishing communication with an external apparatus, when one of the failure and the impossibility is detected in the radiation imaging apparatus operating in a first operation mode capable of taking the radiation image without establishing the communication with the external apparatus.

2. The radiation imaging apparatus according to claim 1, wherein the instructions, when executed by the one or more processors, further cause the radiation imaging apparatus to function as a switch unit configured to switch an operation mode of the radiation imaging apparatus from the first operation mode capable of taking the radiation image without establishing the communication with the external apparatus by not setting the parameter in the radiation imaging apparatus, to the second operation mode, upon the detection by the detection unit.

3. The radiation imaging apparatus according to claim 2, wherein the storage is configured to store the operation mode at a time when power supplied to the radiation imaging apparatus is turned off, and the switch unit is configured to maintain the stored operation mode when the power supply is restarted.

4. The radiation imaging apparatus according to claim 1, wherein the instructions, when executed by the one or more processors, further cause the radiation imaging apparatus to function as a data transmitting unit configured to transmit, to the external apparatus, at least one of imaging failure information that indicates one of the failure in and the impossibility of the imaging, cause information that indicates a cause of one of the failure in and the impossibility of the imaging, storage failure information that indicates one of the failure in and the impossibility of the storing, capacity information that indicates a capacity of the storage, and the radiation image stored in the storage, upon the detection by the detection unit.

5. The radiation imaging apparatus according to claim 1, wherein the instructions, when executed by the one or more processors, further cause the radiation imaging apparatus to function as a communication unit configured to communicate with the external apparatus via a network in a hospital when the communication with the external apparatus is established.

6. The radiation imaging apparatus according to claim 5, wherein the communication in the hospital has a radio frequency band different from a radio frequency band in which the radiation imaging apparatus and the external apparatus directly communicate with each other.

7. A radiation imaging system comprising:
a radiation generator arranged to generate radiation; and
the radiation imaging apparatus according to claim 1.

8. The radiation imaging apparatus according to claim 1, wherein:
the setting unit is capable of further setting a predetermined parameter in the radiation imaging apparatus;
the setting unit is configured to set the predetermined parameter to set the radiation imaging apparatus in the second operation mode, when one of the failure and the impossibility is detected in the radiation imaging apparatus operating in the first operation mode; and the predetermined parameter includes at least one of an identification code of the external apparatus, key information on communication encryption, a type of synchronous mode/asynchronous mode, and an address value of the external apparatus.

9. A radiation imaging apparatus comprising:
a radiation detector arranged to detect radiation;
one or more processors; and
a memory including instructions stored thereon that, when executed by the one or more processors, cause the radiation imaging apparatus to function as:
a generation unit configured to generate a radiation image based on the detected radiation;
a storage configured to store a plurality of radiation images;
a detection unit configured to detect connection to an external apparatus through one of wired communication and wireless communication; and
a setting unit configured to set a parameter for the wireless communication in the radiation imaging apparatus to set the radiation imaging apparatus in a second operation mode of establishing communication with the external apparatus, when the connection is detected in the radiation imaging apparatus operating in a first operation mode capable of taking the radiation image without establishing the communication with the external apparatus.

10. The radiation imaging apparatus according to claim 9, wherein the instructions, when executed by the one or more processors, further cause the radiation imaging apparatus to function as a data transmitting unit configured to transmit, to the external apparatus, radiation images stored in the storage, when the communication with the external apparatus is established.

11. The radiation imaging apparatus according to claim 9, wherein:
the setting unit is capable of further setting a predetermined parameter in the radiation imaging apparatus;
the setting unit is configured to set the predetermined parameter to set the radiation imaging apparatus in the second operation mode, when the connection is detected in the radiation imaging apparatus operating in the first operation mode; and
the predetermined parameter includes at least one of an identification code of the external apparatus, key information on communication encryption, a type of synchronous mode/asynchronous mode, and an address value of the external apparatus.

12. A radiation imaging system comprising:
a radiation generator arranged to generate radiation; and
the radiation imaging apparatus according to claim 9.

13. A radiation imaging method using a radiation imaging apparatus, the method comprising:
detecting radiation;
generating a radiation image based on the detected radiation;
storing a plurality of radiation images;
detecting one of a failure in and impossibility of one of taking of the radiation image and the storing of the radiation image; and
setting a parameter for wireless communication in the radiation imaging apparatus to set the radiation imaging apparatus in a second operation mode of establishing communication with an external apparatus, when one of the failure and the impossibility is detected in the radiation imaging apparatus operating in a first operation mode capable of taking the radiation image without establishing the communication with the external apparatus.

14. A non-transitory computer-readable medium having stored thereon a program that causes a processor to execute each process of the radiation imaging method according to claim 13 when the program is executed by the processor.

15. A radiation imaging method using a radiation imaging apparatus, the method comprising:
   detecting radiation;
   generating a radiation image based on the detected radiation;
   storing a plurality of radiation images;
   detecting connection to an external apparatus through one of wired communication and wireless communication; and
   setting a parameter for the wireless communication in the radiation imaging apparatus to set the radiation imaging apparatus in a second operation mode of establishing communication with the external apparatus, when the connection is detected in the radiation imaging apparatus operating in a first operation mode capable of taking the radiation image without establishing the communication with the external apparatus.

16. A non-transitory computer-readable medium having stored thereon a program that causes a processor to execute each process of the radiation imaging method according to claim 15 when the program is executed by the processor.

* * * * *